United States Patent
Quesnel et al.

(10) Patent No.: US 8,031,341 B2
(45) Date of Patent: Oct. 4, 2011

(54) OPTICAL DETECTION STRUCTURE FOR A PLASMON RESONANCE SENSOR

(75) Inventors: Etienne Quesnel, Grenoble (FR); Pierre Barritault, Grenoble (FR); Gilles Grand, Meylan (FR)

(73) Assignee: Commissariat a l'Energie Atomique, Paris (FR)

( * ) Notice: Subject to any disclaimer, the term of this patent is extended or adjusted under 35 U.S.C. 154(b) by 59 days.

(21) Appl. No.: 12/447,317

(22) PCT Filed: Oct. 31, 2007

(86) PCT No.: PCT/EP2007/061752
§ 371 (c)(1),
(2), (4) Date: Apr. 27, 2009

(87) PCT Pub. No.: WO2008/053016
PCT Pub. Date: May 8, 2008

(65) Prior Publication Data
US 2010/0033725 A1 Feb. 11, 2010

(30) Foreign Application Priority Data
Nov. 3, 2006 (FR) ...................................... 06 54719

(51) Int. Cl.
*G01N 21/55* (2006.01)
(52) U.S. Cl. ...................................................... 356/445
(58) Field of Classification Search ........... 356/445–448
See application file for complete search history.

(56) References Cited

U.S. PATENT DOCUMENTS

| 4,482,779 | A | | 11/1984 | Anderson | |
|---|---|---|---|---|---|
| 5,116,121 | A | * | 5/1992 | Knoll et al. | 356/301 |
| 5,141,311 | A | * | 8/1992 | Hickel et al. | 356/136 |
| 5,991,048 | A | * | 11/1999 | Karlson et al. | 356/445 |
| 5,991,488 | A | | 11/1999 | Salamon et al. | |
| 6,408,123 | B1 | | 6/2002 | Kuroda et al. | |
| 6,421,128 | B1 | * | 7/2002 | Salamon et al. | 356/445 |
| 7,420,682 | B2 | * | 9/2008 | Salamon et al. | 356/445 |

FOREIGN PATENT DOCUMENTS

| JP | 09-250981 A | 9/1997 |
|---|---|---|
| JP | 10-267930 A | 10/1998 |
| JP | 10-274631 A | 10/1998 |
| JP | 2001-215190 A | 8/2001 |

OTHER PUBLICATIONS

Homola et al; "Surface plasmon resonance sensors: review", Sensors and Actuators B, 54, 1999, pp. 3-15.
Patskovsky et al; "Characterization of high refractive index semiconductor films by surface plasmon resonance", Applied Optics, OSA Optical Society of America, Washington D.C., US, vol. 45, No. 25, Sep. 1, 2006, pp. 6640-6645.
Patskovsky et al; "On efficiency of surface plasmon resonance-based absorption sensing with different absorbent materials", Proceeding of the SPIE, The International Society of Optical Engineering, USA, vol. 5327, No. 1, 2004, pp. 102-105.
French Search Report.
PCT Search Report.

* cited by examiner

*Primary Examiner* — Michael P Stafira
(74) *Attorney, Agent, or Firm* — Pearne & Gordon LLP

(57) ABSTRACT

The invention relates to a plasmon resonance optical detection device including a stack of layers comprising:
a metal layer based on a noble metal that will generate said plasmon,
a layer of dielectric material,
at least one first semiconductor bond layer placed between said metal layer and said dielectric layer, said semiconductor layer covering a face of the metal layer.

8 Claims, 5 Drawing Sheets

OPTICAL DETECTION STRUCTURE FOR A PLASMON RESONANCE SENSOR

TECHNICAL DOMAIN

The invention relates to the domain of optical detection based on Plasmon resonance and includes an improved optical detection device by Plasmon resonance and a measurement process using such a device. This invention can be applied particularly to optical measurements including biochemical samples, surrounding atmosphere, gas concentration, moisture content, properties of thin layers, for example with a thickness of the order of one or several nanometers.

PRIOR ART

The document entitled <<Surface Plasmon resonance sensors:review>>, Homola et al., Sensors and actuators B, 54, 3-15, 1999 and document U.S. Pat. No. 5,991,488 present different variants of Plasmon resonance optical detection devices. One example of a Plasmon resonance detection device is illustrated on FIG. 1 and in particular comprises a prism 2 onto which is bonded a thin metal layer 4 based on an adapted metal, for example a noble metal. The thin metal layer 4 will generate a surface Plasmon and will be called a metal <<plasmon>> layer. An incident light radiation 6 that may be monochromatic and with a wavelength located within the domain of the visible or near infrared, is emitted on one face of the prism 2. This light radiation will be deviated by the prism 2 and it will encounter the metal plasmon layer 4. Reflected radiation 8 is measured at the output from the prism 2. The optical response of such a device is illustrated on FIG. 2. A resonance peak on the first curve reference C1 (shown in solid lines) on FIG. 2 represents the fact that for a given angle of incidence, the incident signal is strongly absorbed by the metal plasmon layer 4. Absorption varies depending on the polarisation (s type or p type) of the incident light radiation, and the nature of the metal in the Plasmon layer. This affects the fineness of the resonance peak at the detected signal. When an additional element is put into place, for example an additional thin layer of the order of one or a few nanometers thick on the metal layer 4, the optical response curve of the detector is offset. An example of an optical response of the detector with an additional thin layer is represented by a second curve C2 on FIG. 2. Another example application of such a device is detection of a biological material grafted onto the metal layer 4. The offset depends on the nature and optical properties of the materials used for the prism, the metal layer 4 and the additional thin layer. In a liquid medium, the grafted material can induce a sufficiently large index variation to modify the Plasmon resonance. The detection principle can be placed on a measurement of an angle offset or on a measurement of a variation of the intensity of the signal reflected at a given angle. If an angle offset is measured, the sensitivity of the detection device is greater as the offset between the two curves C1 and C2 increases. If an intensity variation is measured, an attempt is made to obtain the greatest possible range of the curve C2.

Optical transmission measurements can also be made. In this case, according to one variant embodiment of the previously described detection device, the prism can be replaced by a waveguide to which the metal plasmon layer is bonded.

One solution to improve the sensitivity of Plasmon resonance detection devices has been disclosed in document U.S. Pat. No. 5,991,488 and consists of placing one or several dielectric layers in contact with the metal layer that will generate the Plasmon. Such a multi-layered structure is difficult to make, particularly when the metals used to form a metal layer are noble metals such as gold or silver. FIG. 3 illustrated one example of an optical Plasmon resonance detection device with a multi-layer structure that comprises a metal layer 4 based on gold or silver bonded to the prism 2 based on glass or polymer, and a layer of dielectric material 10 bonded to the metal layer 4 that will generate the Plasmon. The dielectric material in layer 10 may for example be an oxide or a fluoride or a selenide or a sulphide, or a nitride. In practice, such a structure is not sufficiently stable, because gold will not bond chemically to a silicon oxide or to a polymer. It is also difficult to bond a silver layer to an element based on silicon oxide or a polymer because silver oxide is thermodynamically not sufficiently stable.

One solution for obtaining a stable detection structure is illustrated on FIG. 4, consisting of using a first metal layer 14 called a <<bond>> layer between the gold or silver based Plasmon metal layer and the layer of dielectric material 10. Another "bond" metal layer 12 may also be provided between the prism 2 and the metal plasmon layer 4. The metal bond layers 12 and 14 are based on a metal that is preferably not noble. The "bond" layers 12 and 14 form a stable stack. The first metal bond layer 14 at the interface with the metal plasmon layer 4 forms a metal alloy, while the oxide bonds at the interface with the layer of dielectric material 10 are formed between the other bond layer 12 and the dielectric layer 10. For example, in the case in which the layer of dielectric material 10 is based on $SiO_2$, the result is Mp—O—Si bonds (where Mp is the metal in the bond layer 12) that assure good bond. The bond layers 12 and 14 are typically based on chromium, or titanium or tantalum, or hafnium. The thickness of these metal bond layers is usually at least two nanometers so that there is no discontinuity. This is a problem with the production of metal bond layers because the metals used to form the bond layers 12 and 14 must be very pure in order to guarantee good bond with the plasmon metal layer. It is known that most metals used to form bond layers, for example such as Cr, Ti, and Hf, tend to trap oxygen atoms. Therefore the deposit of these materials in thin and very pure layers requires deposition processes with a high residual vacuum. Furthermore, the introduction of metal bond layers deteriorates the optical performances of the device. At the working wavelengths usually used in the visible or near infrared, the typical extinction coefficients k of most bond metals are between 2 and 5. The introduction of metal bond layers 12 and 14 has the effect of modifying the optical response by weakening the signal range.

FIG. 5 illustrates the phenomenon of the loss of detection sensitivity due to the metal bond layers, by looking at the results of measurements made on three different structures provided with the same gold layer that will generate the plasmon and the corresponding chromium bond layers between the prism and the gold layer that have different thicknesses in different structures. Curve C3 on FIG. 5 shows measurements made using a first structure provided with 1 nanometer thick chromium-based bond layers, while curves C4 and C5 represent measurements made using a second structure with 2-nanometers thick chromium-based bond layers, and measurements made using a third structure with 3-nanometers thick metal bond layers, respectively. The optical absorption of the chromium bond layer broadens the plasmon resonance peak, that is greater when it is thicker. On FIG. 5, this results in a reduction in the range of the signal, that becomes greater as the thickness of the chromium bond layers increases. The problem that arises is to form a new optical detection device by plasmon resonance that does not have the disadvantages mentioned above.

PRESENTATION OF THE INVENTION

The invention relates firstly to a plasmon resonance optical detection device including a stack of layers comprising:
- a metal <<plasmon>> layer, that will generate said plasmon,
- a layer of dielectric material,
- a first semiconductor bond layer placed between said metal layer and said dielectric layer, said semiconductor layer covering one face of the metal layer.

The layer of dielectric material is a layer that will receive one or several elements to be detected or measured.

One face of the dielectric layer may thus be exposed, the element(s) that are to be detected being placed on this face or put into contact with this face.

Plasmon is a collective oscillation of electrons in a material when the electrons are excited by an appropriate form of energy such as light, which is originally an electromagnetic wave.

The first semiconductor layer enables the layer of dielectric material to bond to the stack without deteriorating the performances of the detector.

The first semiconductor layer may be based on Si or Ge.

According to one possible embodiment, the first semiconductor layer may be not thicker than two nanometers or not thicker than one nanometer or not thicker than 0.5 nanometers.

The metal plasmon layer may be based on a noble metal.

Said stack may comprise a second semiconductor layer on the other face of said metal layer. The second semiconductor layer can act as a bond layer and enables an element based on a dielectric material, for example a prism or a waveguide or a layer or a slide to bond to said stack. Said second bond layer may be based on Si or Ge.

According to a first possible embodiment of the optical detection device, this optical detection device may also comprise at least one prism bonded to said stack.

According to a first possible embodiment, the device may also include a slide bonded to said second semiconductor layer, and placed between the second semiconductor layer and the prism.

According to a second possible embodiment, the plasmon resonance optical detection device may also comprise at least one waveguide bonded to said stack.

According to the second possible embodiment, the detection device may also comprise at least one second layer of dielectric material in contact with said waveguide and with the second semiconductor layer.

BRIEF DESCRIPTION OF THE DRAWINGS

This invention will be better understood after reading the description of example embodiments given purely for information and in no way limitative, with reference to the appended drawings on which.

Identical, similar or equivalent parts of the different figures have the same numeric references to facilitate movement from one figure to another.

The different parts shown on the figures are not necessarily shown at the same scale, to make the figures easier to read.

DETAILED PRESENTATION OF PARTICULAR EMBODIMENTS

Figure 6:
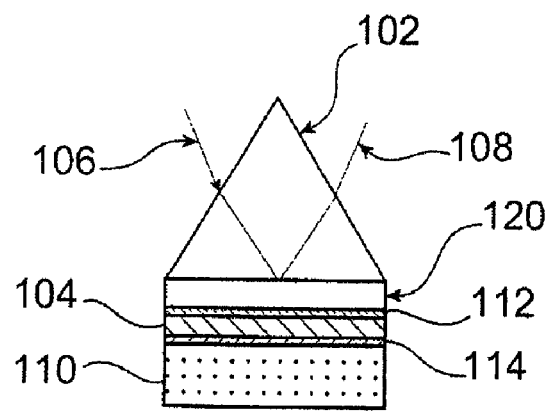
FIG. 6 illustrates an example of a plasmon resonance optical detection device according to the invention.

We will now describe an example of a plasmon resonance optical detection device according to the invention with reference to FIG. 6.

This device comprises a prism 102 that will for example be based on glass or a polymer. A stack comprising at least one metal layer 104 called <<plasmon>> is placed in contact with the prism 102 and will generate a surface plasmon. The metal layer 104 of Plasmon may be based on a noble metal, for example such as silver or gold, and its thickness may for example be between 10 et 100 nanometers, for example it may be of the order of 40 nanometers. Incident light radiation 106 that may be monochromatic, will be emitted on a face of the prism 102. The incident light radiation will be deviated by the prism 102 and it will encounter the metal <<plasmon>> layer 104. Reflected radiation 108 is measured at the output from the prism 102.

The stack also comprises a layer of dielectric material 110, for example based on $SiO_2$, that may for example be between 10 and 100 nanometers thick, for example of the order of 400 nanometers. The metal plasmon layer 104 is located between the prism 102 and the dielectric layer 110. A face of the dielectric layer will come into contact with or will be fitted with one or several elements to be detected, for example biological substances or a gas.

A first semiconductor layer 114 called an <<intermediate>> layer is located between the metal plasmon layer 104 and the dielectric layer 104. The first semiconductor layer 114 is designed to enable the dielectric layer 110 to bond to the stack, while avoiding modifying the optical response of the detector. The first semiconductor layer 114 is in contact with the Plasmon layer 104 and the dielectric layer 110 and may for example be based on Si or Ge. The first semiconductor layer 114 may for example be between 0.4 and 3 nanometers thick.

A second intermediate semiconductor layer 112 may also be provided on the metal layer 104. The second semiconductor layer 112 is in contact with the metal layer 104 and with the prism 102 and may for example be based on Si or Ge. The second semiconductor layer 112 may for example be between 0.3 and 3 nanometers thick, for example of the order of 2.7 nanometers. The semiconductor layers 114 and 112 are preferably continuous, in other words uniformly covering. This continuity of the layers 114, 112 guarantees homogenous bond with the metal plasmon layer 104 and with the layer onto which the second semiconductor layer 112 is bonded. The layers 114 and 112 can be produced without the use of a high vacuum.

The semiconductor layers, particularly the silicon or germanium based layers, may be deposited using known vacuum deposition processes. It is also possible to use <<physical>> deposition techniques by evaporation or sputtering, or <<chemical>> deposition techniques. The vacuum used may for example be between $10^{-5}$ and $10^{-8}$ mbars.

According to one possible embodiment, a microscope slide 120, for example based on glass, may be located between the second semiconductor layer 112 and the prism 102. The slide 120 may be in contact with the second semiconductor layer 112, while an index liquid may be placed between the prism 102 and the slide 120. The prism 102, the slide 120 and the index liquid may have identical refraction indexes, for example of the order of 1.515 for a wavelength of 633 nm. For example, the stack may be selected for detection at a wavelength of the order of 633 nm and an angle of incidence of the order of 50° or 65°.

The material from which the intermediate semiconductor layers 114 and 112 such as silicon or Germanium are made, has the capacity to combine with the metal in the layer 102 such as gold or silver, and optical properties such that an optical detector with an improved sensitivity can be obtained. In particular, the material from which the semiconductor layers 114 and 112 are made has a low extinction coefficient, for example between 0.7 and 0.4 when this material is silicon and the incident radiation 106 is located within a range of visible wavelengths varying from 550 nm and 650 nm.

Throughout this description, the term extinction coefficient will be used to refer to the coefficient k related to the light absorption coefficient α characteristic of a substance or a layer onto which light radiation is applied according to the formula $\alpha=4\Pi k/\lambda$, where $\lambda$ is the wavelength of the light radiation.

Figure 7:
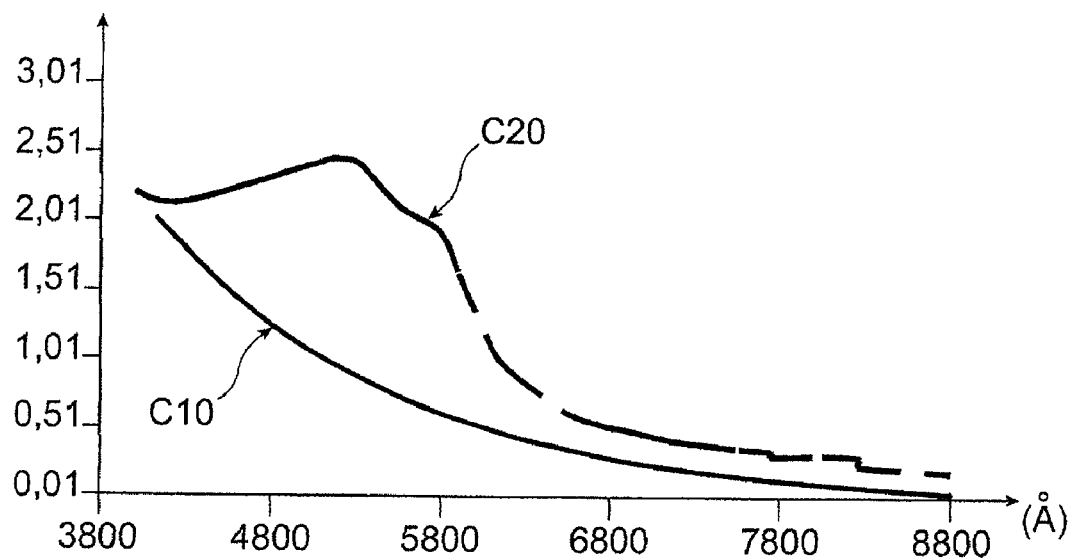
FIG. 7 illustrates curves showing the variation of extinction coefficients for silicon and germanium based layers as a function of a wavelength of incident radiation in the visible and the near infrared.

FIG. 7 contains typical curves of the variation of extinction coefficients for silicon (representative curve C10) and germanium (representative curve C20) as a function of a range of incident radiation wavelengths located in the visible and the near infrared. In the case in which the optical detection device operates with incident light radiation with a wavelength near to the infrared or more than 700 nm, the semiconductor layers 114 and 112 may be based on Si or Ge. In other cases in which the detection device is designed to operate with incident light radiation with a wavelength less than 700 nm, the bond layers 114 and 112 are preferably formed based on silicon.

Figure 1:
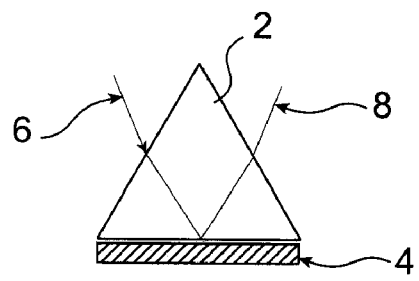
FIG. 1 illustrates a plasmon resonance optical detection device according to prior art, with a metal layer that will generate said plasmon and placed in contact with a prism.
Figure 2:
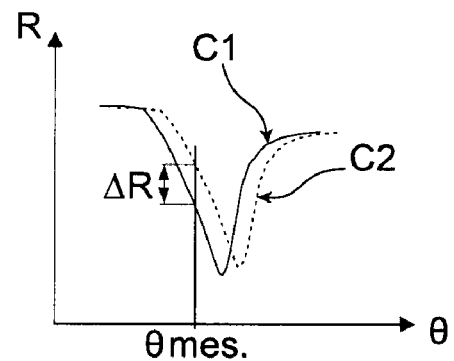
FIG. 2 illustrates examples of optical responses obtained using a device of the type illustrated in FIG. 1.
Figure 3:
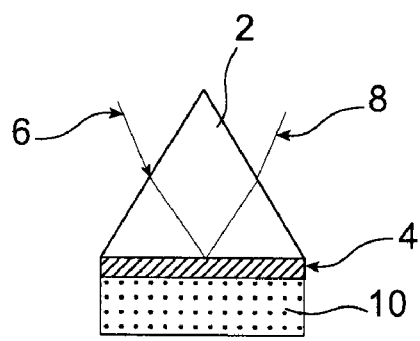
FIG. 3 illustrates a variant embodiment of the device in FIG. 1, in which a layer of dielectric material that will improve the sensitivity of the device is bonded to the metal plasmon layer.
Figure 4:
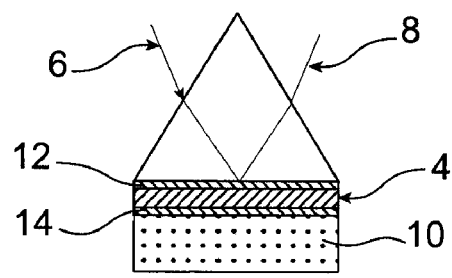
FIG. 4 illustrates a variant for the device in FIG. 3, in which the metal layer is a layer of noble metal, and that comprises metal bond layers between the prism and the layer of noble metal, and between the layer of noble metal and the dielectric layer.
Figure 5:
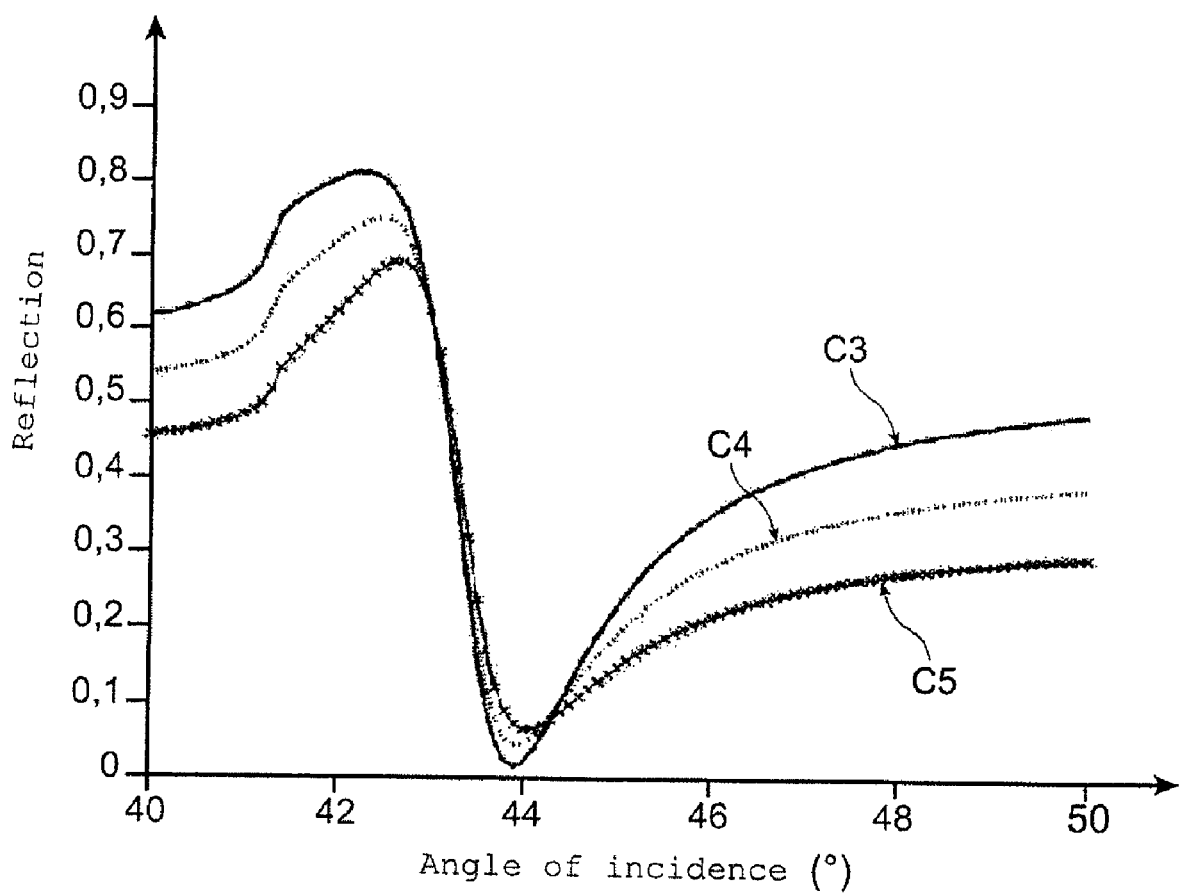
FIG. 5 illustrates optical responses of devices of the type illustrated in FIG. 4, with different thicknesses of metal bond layers.
Figure 8:
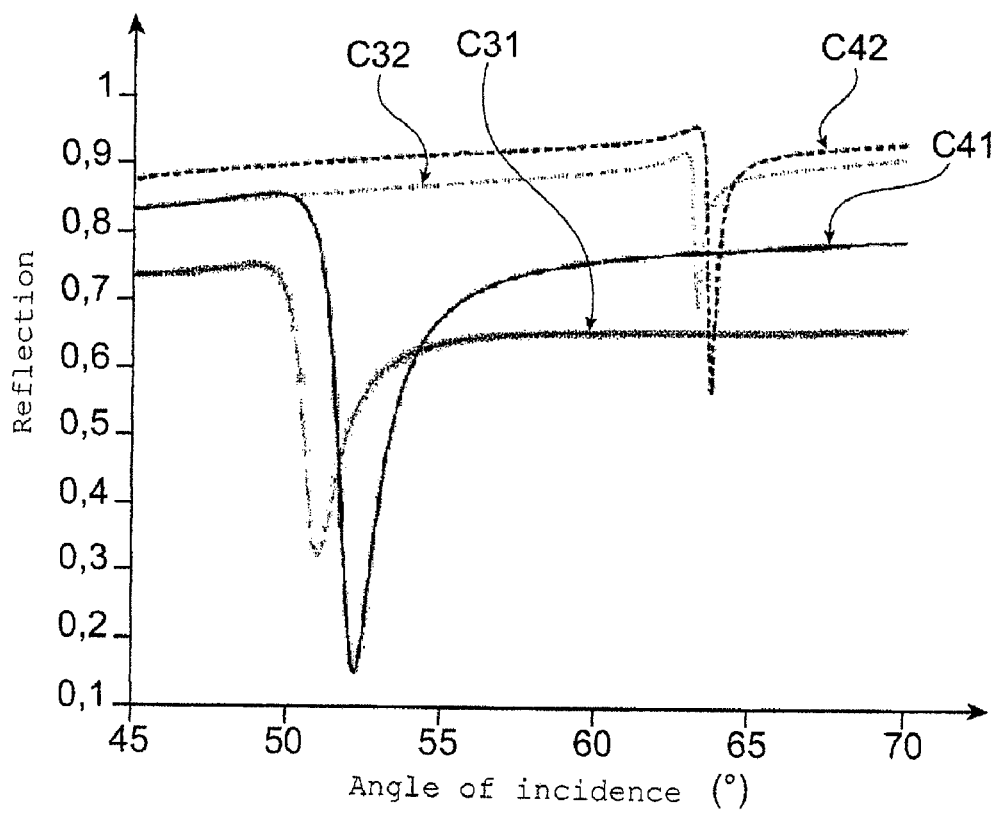
FIG. 8 illustrates the optical responses of an optical detection device according to prior art and an example of an optical detection device according to the invention.

FIG. 8 illustrates differences in detection performances between a plasmon resonance optical detection device according to prior art, and a plasmon resonance optical detection device used according to this invention. Curves C31 and C32 on this FIG. 8 represent optical responses obtained with a detection device used according to the prior art, and a detection device of the type described above with the reference to FIG. 4, for which the metal plasmon layer 4 is made of silver and is of the order of 41.5 nanometers thick, while the bond layers 12 and 14 are chromium layers with thicknesses of the order of 2.47 and 1.42 nanometers respectively, and the dielectric layer 10 is an $SiO_2$ layer of the order of 400.6 nanometers thick. Curve C31 is representative of measurements obtained using incident radiation 6 in s polarisation while curve C32 is obtained using incident radiation 6 in p polarisation. On this FIG. 8, curves C41 and C42 are representative of optical responses obtained using a detection device according to the invention of the type described above with reference to FIG. 6, and in which the metal plasmon layer 104 is a silver layer of the order of 42.8 nanometers thick, the interface layers 102 and 104 are silicon layers with thicknesses of the order of 2.75 nanometers and 1.26 nanometers respectively, and the dielectric layer 110 is an $SiO_2$ layer with a thickness of the order of 406.8 nanometers. Curve C41 is representative of a measurement obtained with an incident radiation 106 polarised according to an s polarisation, while curve C42 is obtained using incident radiation 106 polarised with p polarisation. FIG. 8 shows that the optical response of the device according to the invention has a better range than the detection device according to the prior art. The detector also has better sensitivity in s polarisation than in p polarisation.

Figure 9:
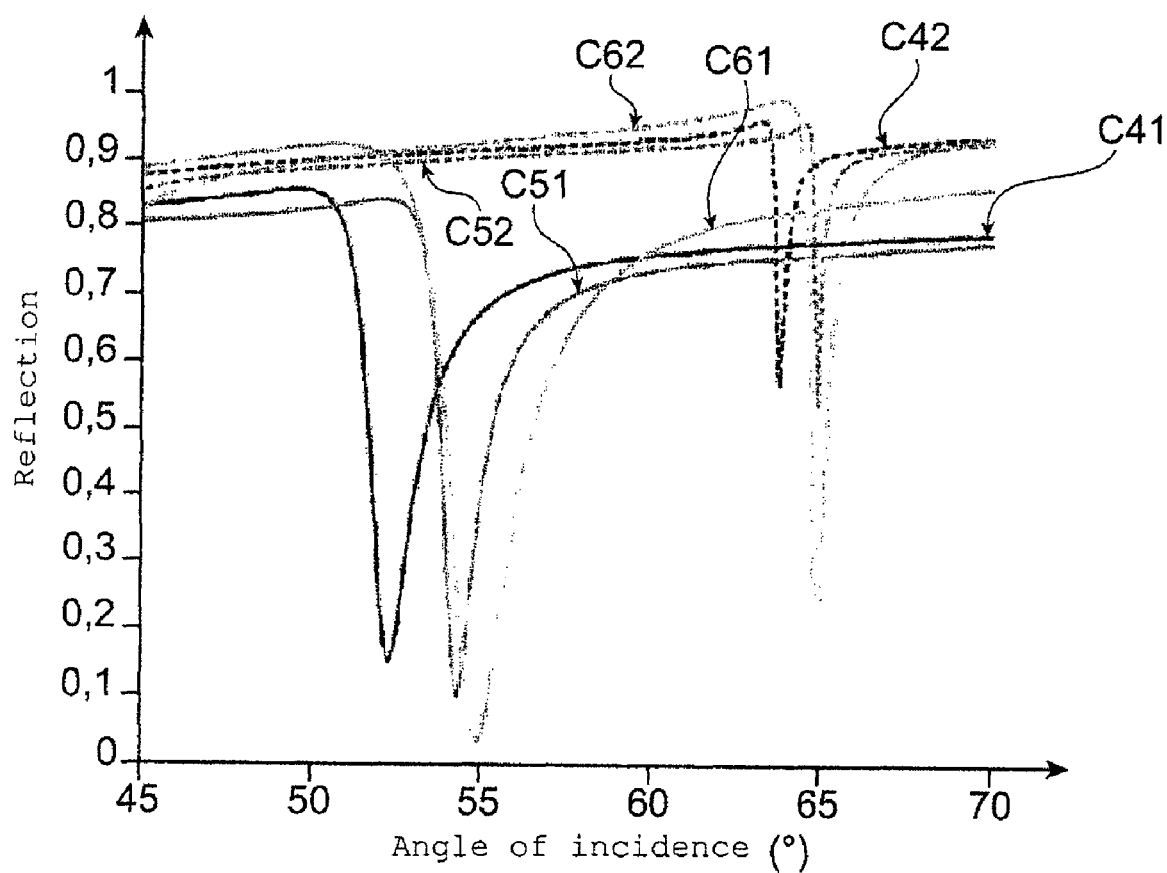
FIG. 9 illustrates different optical responses of examples of optical detection devices according to the invention, each of which has a semiconductor layer bonded to the metal plasmon layer.

FIG. 9 shows curves C41 and C42 and other curves C51, C52, C61, C62 of optical responses. Curves C51 and C52 on FIG. 9 are representative of optical responses obtained using a detection device according to the invention of the type described above with reference to FIG. 6, in which the metal plasmon layer 104 is a silver layer of the order of 43.2 nanometers thick, the interface layers 102 and 104 are silicon layers with thicknesses of 2.75 and 0.85 nanometers respectively, and the dielectric layer 110 is an $SiO_2$ layer of the order of 434.5 nanometers thick. Curves C61 and C62 represent optical responses obtained using a detection device according to the invention of the type described above with reference to FIG. 6, and in which the metal plasmon layer 104 is a silver layer of the order of 36.5 nanometers thick, the interface layers 102 and 104 are silicon layers with thicknesses of the order of 2.71 and 0.46 nanometers respectively, and the dielectric layer 110 is an $SiO_2$ layer of the order of 401.2 nanometers thick. Curves C51 and C61 are representative of measurements obtained using polarised incident radiation 106 using s polarisation, while curves C52 and C62 are representative of measurements obtained using polarised incident radiation 106 using p polarisation. The curves in FIG. 9 show that the performances of the detector in terms of measured signal range improves as the thickness of the semiconductor layer 104 between the metal plasmon layer 104 and the dielectric layer 110 becomes smaller.

Figure 10:
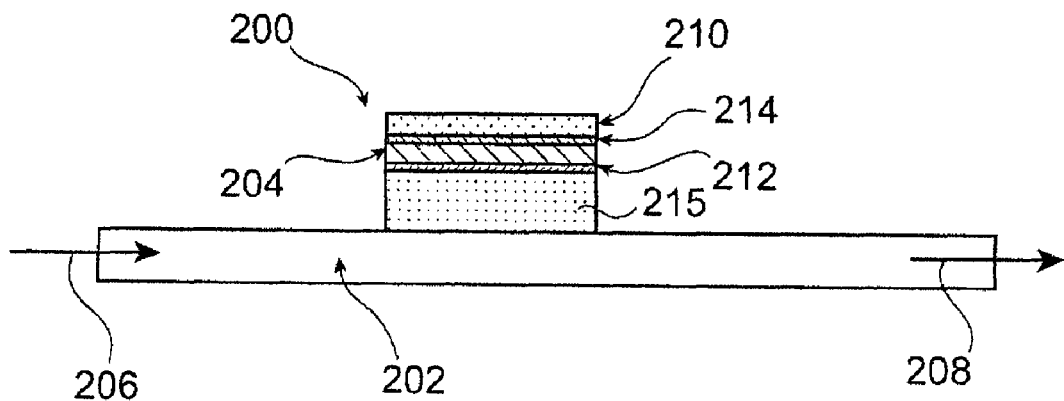
FIG. 10 illustrates a variant plasmon resonance optical detection device according to the invention, in which the stack comprising the metal layer that will generate the plasmon is bonded to a waveguide.

FIG. 10 illustrates another example of plasmon resonance optical detection device. In this example, the device is designed to measure in "transmission" and it comprises a waveguide 202 that may for example be based on glass or a polymer. A stack is placed on the waveguide 202 comprising a metal layer 204 that will generate the plasmon, and based on a noble metal, for example such as silver or gold and for example between 10 and 100 nanometers thick, for example of the order of 40 nanometers. The stack also comprises a first layer 210 of dielectric material, for example based on $SiO_2$ and that may for example be between 10 and 100 nanometers thick, for example of the order of 40 nanometers. A first semiconductor layer 214 is located between the metal plasmon layer 204 and the first dielectric layer 210. The first intermediate semiconductor layer 214 is designed to enable the first dielectric layer 210 to bond to the stack without causing any alteration to the optical response of the detector. The first semiconductor layer 214 may for example be based on Si or Ge. The first semiconductor layer 114 may be between 0.4 and 3 nanometers thick, for example of the order of 2 nanometers. A second semiconductor layer 112 may also be provided on the metal layer 104. The second semiconductor layer 112 may be between 0.4 and 3 nanometers thick, for example of the order of 1 nanometer. The second semiconductor layer 114 is in contact with the metal layer 104 and a second layer of dielectric material 215 in contact with the waveguide 202. The second layer 215 of dielectric material is also selected to allow the first dielectric layer 210 to bond to the stack while avoiding any alteration to the optical response of the detector. The second layer 215 of dielectric material may for example be based on $SiO_2$ and its thickness may for example be between 10 and 1000 nanometers, for example of the order of 800 nanometers.

Figure 11A:
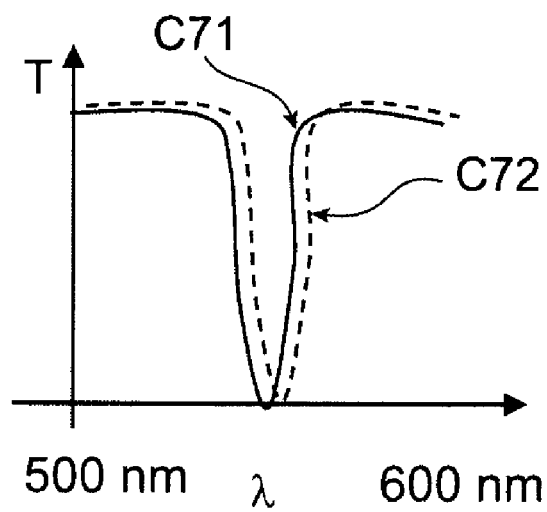
FIGS. 11A and 11B illustrate examples of optical response curves of a device of the type illustrated in FIG. 10.

In this case, the measurement is a measurement of a light signal 208 transmitted at the output from the waveguide 202, as a function of the wavelength of light rays 206 injected into the waveguide 202. For this type of detection, the plasmon resonance phenomenon induces a drop in the signal transmission, for which the wavelength position depends on the nature and structure of the stack formed by the second layer of dielectric material 215, the first semiconductor layer 214, the metal layer 204 generating the plasmon, the first semiconductor layer 214, and the first layer of dielectric material 210. A modification to the surface index on the dielectric layer 210 at the top of the structure causes a shift in the transmission spectrum. This shift is illustrated on FIG. 11A by transmitted signal curves C71 and C72 representing measurements made without the presence of an additional element on the dielectric layer 210, and measurements made with an additional element modifying the surface index, respectively.

Figure 11B:
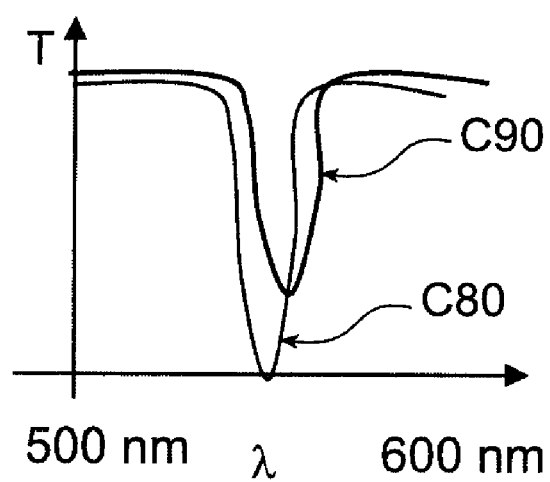

FIG. 11B shows a curve C80 representative of a transmitted signal 208 obtained with a device like that described above with reference to FIG. 10 and in which the interface layers 212 and 214 are based on silicon, and another curve C90 representative of a transmitted signal obtained with a similar device, but in which the layers 214 and 212 are replaced by chromium based layers. As shown on this FIG. 11B, the detection performance in terms of transmitted signal amplitude is better with a device provided with semiconductor interface layers 212 and 214.

Note that the second dielectric layer 215 optically adapts the stack and waveguide such that light rays 206 can enter into the stack as far as possible to create a maximum electromagnetic field in the plasmon layer 204. The second dielectric layer 215 makes impedance matching between the stack and the waveguide possible.

Either of the devices described above may be integrated for example into a measurement sensor for samples of biochemicals or the surrounding atmosphere, or to measure a gas concentration or moisture content.

A device according to this invention includes a so-called metal plasmon layer. This metal layer may possibly be composed of a stack of several metal layers with different compositions. Similarly, each of the dielectric layers used may be composed of a stack of several dielectric layers with different natures. The same is true for the semiconductor bond layer(s).

The invention claimed is:

1. Plasmon resonance optical detection device including a stack comprising:
   a metal plasmon layer, that will generate said plasmon,
   a layer of dielectric material that is adapted to receive one or several elements to be detected, and
   a semiconductor bond layer of a semiconducting silicon composition or a semiconducting germanium composition placed between said metal layer and said dielectric layer, said semiconductor layer covering one face of the metal layer.

2. Plasmon resonance optical detection device according to claim 1, said stack comprising also a second semiconductor layer on a face of said plasmon metal layer opposite a face provided with said semiconductor bond layer.

3. Plasmon resonance optical detection device according to claim 1, wherein the semiconductor bond layer comprises a thickness of less than 2 nanometers.

4. Plasmon resonance optical detection device according to claim 2, wherein said second semiconductor layer is formed from semiconducting silicon or semiconducting germanium.

5. Plasmon resonance optical detection device according to claim 1, also comprising at least one prism bonded to said stack.

6. Plasmon resonance optical detection device according to claim 5, in which said stack comprises at least one second semiconductor layer on a face of said metal layer opposite a face provided with said semiconductor bond layer, the detection device also comprising a slide bonded to said second semiconductor layer and placed between this second semiconductor layer and the prism.

7. Plasmon resonance optical detection device according to claim 1, also comprising at least one waveguide bonded to said stack.

8. Plasmon resonance detection device according to claim 7, in which at least a second semiconductor layer covers a face of said metal layer opposite a face provided with said semiconductor bond layer, the device comprising at least one second layer of dielectric material in contact with said waveguide and with said second semiconductor layer.

* * * * *